(12) United States Patent
Knochel et al.

(10) Patent No.: US 7,009,065 B2
(45) Date of Patent: Mar. 7, 2006

(54) FERROCENYL LIGANDS AND THE USE THEREOF IN CATALYSIS

(75) Inventors: Paul Knochel, Munich (DE); Matthias Lotz, Munich (DE); Axel Monsees, Frankfurt (DE); Thomas Riermeier, Nidderau-Ostheim (DE); Renat Kadyrov, Frankfurt (DE); Juan Jose Almena Perea, Hanau (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/506,255

(22) PCT Filed: Mar. 10, 2003

(86) PCT No.: PCT/EP03/02429

§ 371 (c)(1),
(2), (4) Date: Jun. 28, 2005

(87) PCT Pub. No.: WO03/076451

PCT Pub. Date: Sep. 18, 2003

(65) Prior Publication Data

US 2005/0234253 A1    Oct. 20, 2005

(30) Foreign Application Priority Data

Mar. 13, 2002 (DE) .................... 102 11 250

(51) Int. Cl.
*C07F 17/00* (2006.01)
*B01J 31/00* (2006.01)
*C07C 5/02* (2006.01)

(52) U.S. Cl. .............. 556/14; 556/28; 556/136; 556/143; 502/154; 502/155; 526/93; 568/862; 585/275

(58) Field of Classification Search ............ 556/14, 556/28, 136, 143; 502/154, 155; 526/93; 568/862; 585/275
See application file for complete search history.

(56) References Cited

U.S. PATENT DOCUMENTS

| | | | |
|---|---|---|---|
| 5,856,540 A | 1/1999 | Jendralla | 556/21 |
| 6,191,284 B1 * | 2/2001 | Knochel et al. | 548/42 |
| 6,777,567 B1 * | 8/2004 | Weissensteiner et al. | 556/16 |
| 6,939,981 B1 * | 9/2005 | Boaz | 556/14 |

OTHER PUBLICATIONS

Bronco et al., Helvetica Chimica Acta, vol. 78, No. 4, pp. 883-886 (1995).*
Lotz, Matthias et al. "Facile axial chirality control by using a precursor with central chirality. Application to the preparation of new axially chiral diphosphine complexes for asymmetric catalysis", Chem. Commun., vol. 21, pp. 2546-2547, XP002244213 2002.

* cited by examiner

*Primary Examiner*—Porfririo Nazario-Gonzalez
(74) *Attorney, Agent, or Firm*—Oblon, Spivak, McClelland, Maier & Neustadt, P.C.

(57) ABSTRACT

The invention relates to bidentate organophosphorous ferrocenyl ligands containing ligands of formula (I), to their complex compounds and to their utilization in catalytic processes.

20 Claims, No Drawings

FERROCENYL LIGANDS AND THE USE THEREOF IN CATALYSIS

DESCRIPTION

The present invention relates to bidentate organophosphorus ferrocenyl ligands, their complex compounds, as well as their use in catalytic processes.

Trisubstituted organophosphorus compounds are extremely important as ligands in homogeneous catalysis. By varying the substituents on the phosphorus atom in such compounds the electronic and steric properties of the phosphorus ligand can be purposefully influenced, so that selectivity and activity in homogeneous catalytic processes can be controlled.

The importance of the hitherto known phosphorus ligands is reflected in their multifarious structures. The ligands may be classified for example according to substance classes. Examples of such substance classes are trialkyl and triaryl phosphines, phosphites, phosphinites, phosphonites, aminophosphanes, etc. This classification according to substance classes is particularly useful for describing the electronic properties of a ligand.

In addition it is also possible to classify phosphorus ligands according to their symmetry properties or according to the dentativeness of the ligands. This classification takes into account in particular the stability, activity and potential stereoselectivity of metal complexes with phosphorus ligands as catalyst precursors or catalysts.

In addition to the widely used $C_2$-symmetrical bidentate ligand systems such as DUPHOS, DIOP, BINAP or DEGUPHOS, attention is increasing being focused on asymmetrical bidentate organophosphorus ligands in the formulation of new asymmetric catalytic processes. Important examples are the large class of versatile chiral ferrocenyl phosphine ligands such as e.g. JOSIPHOS, the aminophosphine-phosphinite ligands such as PINDOPHOS or DPAMPP, which are successfully used in particular in the asymmetric hydrogenation of olefins, or the phosphine-phosphite ligands such as BINAPHOS or BIPHEMPHOS, which are used in the asymmetric hydroformylation of olefins. An important aspect of the success of these classes of compounds is ascribed to the creation of a particularly asymmetrical environment of the metal centre by these ligand systems.

This demonstrates that the development of new ligands plays a decisive role in improving catalytic processes. For this reason there is furthermore a need for new enantiomer-enriched chiral ligands whose electronic and stereochemical properties can be optimally matched to the respective catalysis problem.

The object of the present invention is accordingly to make available chiral ligands that can be varied stereochemically and electronically in order to be able to provide the optimal, tailor-made ligands for a specific asymmetric catalysis.

The present invention describes novel, asymmetrical, bidentate and chiral phosphorus ligand systems that combine in a unique manner the most important features listed above for effective asymmetric induction. A particular advantage in this connection is that they create a highly asymmetric co-ordination sphere with organophosphorus donors that can be modified independently of one another.

The present invention accordingly relates to unsymmetric bidentate organophosphorus ligands of the formula (I) with two trivalent phosphorus groups, which are joined to one another via a ferrocenyl unit,

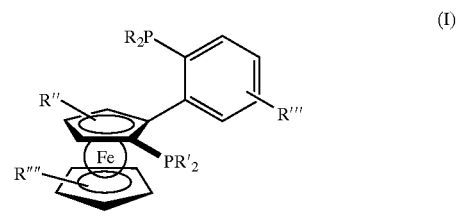

wherein

R, R' independently of one another may denote for each of the two substituents R or R' a radical selected from the group $C_1$–$C_{24}$ alkyl, $C_2$–$C_{24}$ alkenyl, $C_3$–$C_8$ cycloalkyl, $C_3$–$C_8$ cycloalkenyl, $C_6$–$C_{14}$ aryl, phenyl, naphthyl, fluorenyl, furfuryl, 1-adamantyl, $C_2$–$C_{13}$ heteroaryl, in which the number of heteroatoms, in particular from the group N, O, S, may be 1 to 4, in which the cyclic aliphatic or aromatic radicals are preferably 5- to 7-membered rings, and in which the aforementioned R and R' may in each case be monosubstituted or polysubstituted, wherein these substituents may independently of one another be selected from the group $C_1$–$C_{12}$ alkyl, $C_2$–$C_{12}$ alkenyl, $C_1$–$C_{10}$ haloalkyl, $C_3$–$C_8$ cycloalkyl, $C_3$–$C_8$ cycloalkenyl, $C_2$–$C_9$ heteroalkyl, $C_1$–$C_9$ heteroalkenyl, $C_6$–$C_{14}$ aryl, phenyl, naphthyl, fluorenyl, $C_2$–$C_7$ heteroaryl, in which the number of heteroatoms, in particular from the group N, O, S, may be 1 to 4, $C_1$–$C_{10}$ alkoxy, $C_1$–$C_9$ trihalomethylalkyl, trifluoromethyl, trichloromethyl, fluoro, chloro, hydroxy, $C_1$–$C_8$ substituted amino of the forms mono-, di-, tri- $C_1$–$C_8$ alkylamino or $C_2$–$C_8$ alkenylamino or mono-, di-, tri- $C_6$–$C_8$ arylamino or carboxyl, carboxylato of the form COOR" where R" denotes a monovalent cation or a $C_1$–$C_8$ alkyl, $C_1$–$C_8$ acyloxy, tri- $C_1$–$C_6$ alkylsilyl, and in which two of these substituents may also be bridged, and wherein R", R'", R"" independently of one another may for each substituent R", R'" or R"" denote a radical selected from the group hydrogen, $C_1$–$C_{24}$ alkyl, $C_2$–$C_{24}$ alkenyl, $C_3$–$C_8$ cycloalkyl, $C_3$–$C_8$ cycloalkenyl, $C_1$–$C_{10}$ alkoxy, $C_1$–$C_9$ trihalomethylalkyl, trifluoromethyl, trichloromethyl, fluoro, chloro, hydroxy, $C_1$–$C_8$ substituted amino of the forms mono-, di-, tri- $C_1$–$C_8$ alkylamino or $C_2$–$C_8$ alkenylamino or mono-, di-, tri- $C_6$–$C_8$ arylamino or carboxyl, carboxylato of the form COOR"", where R"" denotes a monovalent cation or a $C_1$–$C_8$ alkyl, or $C_1$–$C_8$ acyloxy, tri- $C_1$–$C_6$ alkylsilyl, and where two of these substituents may also be bridged.

In a preferred embodiment R or R' may in this connection independently of one another denote phenyl, furfuryl, 3,5-dimethylphenyl, 4-methylphenyl, 2-methylphenyl, 4-methoxyphenyl, 3,5-bis(trifluoromethyl)phenyl, cyclohexyl, tert.-butyl, n-butyl, 2-propyl, ethyl, methyl or 1-adamantyl.

The invention also relates to complex compounds that contain such a chiral ligand system of the formula (I) with at least one metal.

Preferably R, R', R'" and R"" independently of one another denote an alkyl, alkenyl, haloalkyl, cycloalkyl, cycloalkenyl, aryl or heteroaryl radical containing 1 to 12 atoms, in which these radicals may in each case be mono-substituted or polysubstituted. Preferably the radicals R, R', R'" and R"" are in this connection substituted by $C_1$–$C_{10}$ alkyl, $C_2$–$C_{10}$ alkenyl, $C_1$–$C_{10}$ haloalkyl, $C_3$–$C_8$ cycloalkyl, $C_3$–$C_8$ cycloalkenyl, $C_6$–$C_{14}$ aryl, $C_2$–$C_7$ heteroaryl, $C_1$–$C_{10}$ alkoxy, halogen or hydroxy.

From the group of alkyl substituents there may preferably be mentioned methyl, ethyl, n-propyl, 1-methylethyl, n-butyl, 1-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, n-heptyl, n-octyl, n-nonyl, n-decyl.

Among the cyclic alkyl substituents, particularly preferred are substituted and unsubstituted cyclopentyl, cyclohexyl and cycloheptyl.

As alkenyl radicals there may preferably be mentioned vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl, 2-heptenyl, 1-octenyl or 2-octenyl. Particularly preferred among the cyclic alkenyl substituents are cyclopentenyl, cyclohexenyl, cycloheptenyl and norbornyl.

Among aryl substituents in R and R' there are particularly preferred phenyl, furfuryl, 2-alkylphenyl, 3-alkylphenyl, 4-alkylphenyl, 2,6-dialkylphenyl, 3,5-dialkylphenyl, 3,4,5-trialkylphenyl, 2-alkoxyphenyl, 3-alkoxyphenyl, 4-alkoxyphenyl, 2,6-dialkoxyphenyl, 3,5-dialkoxyphenyl, 3,4,5-trialkoxyphenyl, 3,5-dialkyl-4-alkoxyphenyl, 3,5-dialkyl-4-dialkylaminophenyl, 4-dialkylamino, in which the aforementioned alkyl and alkoxy groups in each case preferably contain 1 to 6 carbon atoms, 3,5-trifluoromethyl, 4-trifluoromethyl, 2-sulfonyl, 3-sulfonyl, 4-sulfonyl, and monohalogenated to tetrahalogenated phenyl and naphthyl. Preferred halogen substituents are F, Cl, Br, I, particularly preferred being F and Cl.

All haloalkyl and/or haloaryl groups preferably have the general formulae $CHal_3$, $CH_2CHal_3$, $C_2Hal_5$, in which Hal may in particular denote F and Cl. Particularly preferred are haloalkyl and/or haloaryl groups of the formula $CF_3$.

Finally, ligand systems of the formula (I) in which one enantiomer is enriched are preferred as optically active ligand systems. Particularly preferred are ligand systems in which the enantiomer enrichment exceeds 90%, preferably 99%.

The ligands according to the invention may be prepared according to the general synthesis procedure described hereinafter.

In the first preparation step ferrocene is reacted by a method of Kagan et al. (*J. Org. Chem.* 1995, 60, 2502) to form chiral ferrocenyl-sulfoxide A. In order to introduce the aromatic group and the first phosphorus-containing group, the ferrocenyl ring is lithiated and transmetallated in the presence of a lithium base. The coupling to form the corresponding compound B takes place in the presence of a palladium catalyst.

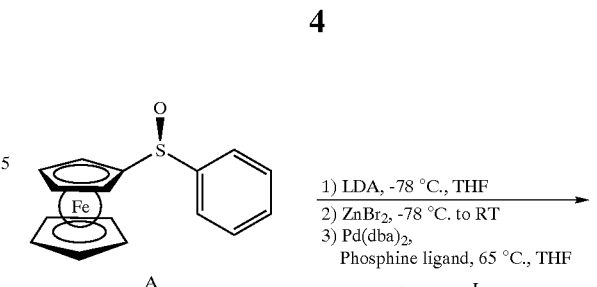

The sulfoxide group can be substituted by the second phosphorus-containing group in the presence of a strong lithium base. The ligand C according to the invention is thereby obtained.

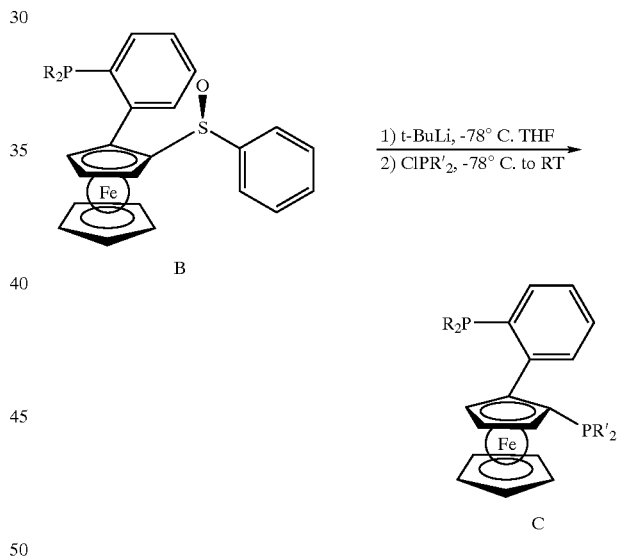

The bidentate organophosphorus ferrocenyl ligands according to the invention can be obtained in good yields by means of this process. A further major advantage of the process is its tolerance to educts that are substituted on the phenyl ring or on the ferrocenyl radical. In this way the flexibility of the ligand system can easily be varied, whereby the asymmetric induction can be controlled.

By using the claimed ligands reactions can easily be carried out with metals to form complex compounds that contain at least one metal atom or ion, preferably a transition metal atom or ion, preferably from the group palladium, platinum, rhodium, ruthenium, osmium, iridium, cobalt, nickel and/or copper.

The preparation of these metal-ligand complex compounds may take place in situ by reacting a metal salt or a corresponding precomplex with the ligands of the general formula (I). In addition, a metal-ligand complex compound can be obtained by reacting a metal salt or a corresponding precomplex with the ligands of the general formula (I) followed by separation.

Examples of metal salts are metal chlorides, bromides, iodides, cyanides, nitrates, acetates, acetylacetonates, hexafluoroacetylacetonates, tetrafluoroborates, perfluoroacetates or triflates, in particular of palladium, platinum, rhodium, ruthenium, osmium, iridium, cobalt, nickel and/or copper.

Examples of suitable precomplexes are:
cyclooctadiene palladium chloride, cyclooctadiene palladium iodide, 1,5-hexadiene palladium chloride, 1,5-hexadiene palladium iodide, bis(dibenzylideneacetone)palladium, bis(acetonitrile)palladium(II) chloride, bis(acetonitrile)palladium(II) bromide, bis(benzonitrile)palladium(II) chloride, bis(benzonitrile)palladium(II) bromide, bis(benzonitrile)palladium(II) iodide, bis(allyl)palladium, bis(methallyl)palladium, allyl palladium chloride dimer, methallyl palladium chloride dimer, tetramethyl ethylenediamine palladium dichloride, tetramethylethylenediamine palladium dibromide, tetramethylethylenediamine palladium diiodide, tetramethylethylenediamine palladium dimethyl, cyclooctadiene platinum chloride, cyclooctadiene platinum iodide, 1,5-hexadiene platinum chloride, 1,5-hexadiene platinum iodide, bis(cyclooctadiene)platinum, potassium(ethylenetrichloroplatinate)cyclooctadiene rhodium(I) chloride dimer, norbornadiene rhodium(I) chloride dimer, 1,5-hexadiene rhodium(I)chloride dimer, tris(triphenylphosphane)rhodium(I) chloride, hydridocarbonyltris(triphenylphosphane)rhodium(I) chloride, bis(cyclooctadiene)rhodium(I) perchlorate, bis(cyclooctadiene)rhodium(I) tetrafluoroborate, bis(cyclooctadiene)rhodium(I) triflate, bis(acetonitrilecyclooctadiene)rhodium(I)perchlorate, bis(acetonitrilecyclooctadiene)rhodium(I)tetrafluoroborate, bis(acetonitrilecyclooctadiene)rhodium(I)triflate, cyclopentadiene rhodium(III) chloride dimer, pentamethyl cyclopentadiene rhodium(III) chloride dimer, (cyclooctadiene)Ru(allyl)$_2$, ((cyclooctadiene)Ru)$_2$(acetate)$_4$, ((cyclooctadiene)Ru)$_2$(trifluoroacetate)$_4$, RuCl$_2$(arene)dimer, tris(triphenylphosphane)ruthenium(II) chloride, cyclooctadiene ruthenium(II) chloride, OsCl$_2$(arene)dimer, cyclooctadiene iridium(I) chloride dimer, bis(cyclooctene)iridium(I) chloride dimer, bis(cyclooctadiene)nickel, (cyclododecatriene)nickel, tris(norbornene)nickel, nickel tetracarbonyl, nickel(II) acetylacetonate, (arene)copper triflate, (arene) copper perchlorate, (arene)copper trifluoroacetate, cobalt carbonyl.

The complex compounds based on one or more metals of the metallic elements, in particular of the group comprising Ru, Co, Rh, Ir, Ni, Pd, Pt, Cu, may already be catalysts or may be used for the preparation of catalysts based on one or more metals of the metallic elements, in particular of the group comprising Ru, Co, Rh, Ir, Pd, Pt, Cu.

In addition to the in situ preparation of catalysts with ligands of the formula (I) in the reaction mixture to be reacted, the metal-ligand complex compound may also be obtained by reacting a metal salt or a corresponding precomplex with the ligands of the general formula (I) and subsequent separation. The formation of such a complex compound preferably takes place in a one-pot reaction while stirring at elevated temperature. Catalytically active complex compounds may in this connection also be prepared directly in the reaction batch of the planned catalytic conversion.

The ligands of the general formula (I) may be used as ligands to metals in asymmetric, metal-catalysed reactions, such as e.g. hydrogenation, hydroformylation, in rearrangements, allylic alkylation, cyclopropanation, hydrosilylation, in hydride transfers, in hydroboronations, in hydrocyanations, in hydrocarboxylations, in aldol reactions or in the Heck reaction, as well as in polymerisations. The ligands are in particular especially suitable for asymmetric reactions.

The complexes according to the invention are particularly suitable in the asymmetric hydrogenation of C=C, C=O or C=N bonds, in which they exhibit high activities and selectivities, as well as in asymmetric hydroformylation. It has proved particularly advantageous in this case that the ligands of the general formula (I) can, due to the ease with which they can be widely modified, be sterically and electronically ideally matched to the respective substrate and catalytic reaction.

EXAMPLES OF IMPLEMENTATION

General Information

Reactions involving air-sensitive compounds were carried out in an argon-filled glove box or in standard Schlenk tubes. Solvents—tetrahydrofuran (THF), diethyl ether and dichloromethane—were degassed and rendered anhydrous by means of a solvent drying unit (Innovative Technologies) by filtration through a column packed with activated aluminium oxide, while toluene and pentane were in addition freed from oxygen by passage through a column packed with a copper catalyst.

The following examples serve to illustrate the invention, though in no way do they represent a restriction of the latter.

Example 1

(SFc,SS)-(p-tolylsulfinyl)-2-[(o-diphenylphosphino)phenyl]ferrocene (S)-ferrocenyl-p-tolyl sulfoxide (793 mg, 2.45 mmole) was dissolved in THF (15 ml) in a 100 ml round-bottomed flask with an argon inlet and the solution was cooled to −78° C. Lithium diisopropylamine solution (1.35 ml, 2.70 mmole; 2.0 M in THF) was then slowly added. After stirring for 30 minutes at −78° C. zinc bromide solution (2.70 ml, 3.51 mmole; 1.3 M in THF) was added dropwise and the reaction solution was stirred for 1 hour at RT. The solvent was removed in vacuo and the residue was dissolved in 10 ml of THF. Pd (dba)2 (61.2 mg, 5 mole %) and trifuryl phosphine (49.2 mg (10 mole %) were dissolved in THF (2 ml) in a 50 ml round-bottomed flask with an argon inlet and stirred for 10 minutes. 1-iodo-2-(diphenylphosphino)benzene (633 mg, 1.63 mmole) dissolved in THF (3 ml) was then added dropwise and stirring was continued for 10 minutes. After the addition of the solution of the zinc compound the reaction mixture was stirred for 14 hours at 65° C. The reaction was then quenched with saturated ammonium chloride solution, the organic phase was separated, and the aqueous phase was extracted with diethyl ether (3×50 ml). The combined organic phases were washed with sodium chloride solution (20 ml), dried over magnesium sulfate, filtered, and the solvent was distilled off on a rotary evaporator. The crude product was purified by column chromatography (n-pentane/diethyl ether 1:2). The sulfoxide (707 mg, 1.21 mmole, 74%) was obtained as a yellow-brown solid (m.p. 198° C.)

$^1$H-NMR (CDCl$_3$, 300 MHz): 8.29–8.24 (m, 1 H), 7.37–7.06 (m, 14 H), 6.82–6.71 (m, 3 H)4.40–4.38 (m, 1 H), 4.25–4.23 (m, 1 H), 4.20 (s, 5 H), 4.08–4.05 (m, 1 H), 2.29 (s, 3 H). $^{13}$C-NMR (CDCl$_3$, 75 MHz): 140.91, 140.22, 140.15, 139.84, 138.34–137.51 (m), 134.39 (d, J=4.6 Hz), 133.94–133.28 (m), 128.96–127.52 (m), 124.74, 94.90, 90.51 (d, J=10.0 Hz), 73.97 (d, J=11.0 Hz), 70.84, 69.80, 67.68, 21.34. $^{31}$P-NMR (CDCl$_3$, 81 MHz): −13.12.

Example 2

(S)-2-[(o-diphenylphosphino)phenyl]-1-diphenyl-phosphinoferrocene (Ligand 1)

Sulfoxide (300 mg, 0.51 mmole) was dissolved in THF (8 ml) in a 50 ml round-bottomed flask with an argon inlet and the solution was cooled to −78° C. t-BuLi (0.64 ml, 1.03 mmole, 1.6 M in hexane) was then slowly added dropwise and stirred for 5 minutes at −78° C. Chlorodiphenylphosphane (0.32 ml, 1.80 mmole) was added dropwise, the cooling bath was removed, and the reaction mixture was stirred for 30 minutes at RT. After quenching with saturated ammonium chloride solution (20 ml) the organic phase was separated and the aqueous phase was extracted with diethyl ether (2×50 ml). The combined organic phases were washed with sodium chloride solution (20 ml), dried over magnesium sulfate, filtered, and the solvent was distilled off on a rotary evaporator. The crude product was purified by column chromatography (n-pentane/diethyl ether 50:1). The diphosphane (260 mg, 0.41 mmole, 81%) was obtained as a yellow solid (m.p.: 187° C.).

$^1$H-NMR (CDCl$_3$, 300 MHz): 8.36–8.32 (m, 1 H), 7.56–7.50 (m, 2 H), 7.37–7.27 (m, 9 H), 7.18–7.12 (m, 2 H), 7.08–6.96 (m, 7 H), 6.81–6.77 (m, 1 H), 6.67–6.61 (m, 2 H), 4.28–4.26 (m, 1 H), 4.19–4.16 (m, 1 H), 3.95 (s, 5 H), 3.76–3.75 (m, 1 H). $^{13}$C-NMR (CDCl$_3$, 75 MHz): 142.74 (d, J=30.8 Hz), 139.36 (d, J=4.1 Hz), 139.19 (d, J=6.7 Hz), 138.39 (d, J=9.4 Hz), 137.94 (d, J=12.9 Hz), 137.39 (d, J=14.3 Hz), 135.35–127.04 (m), 95.67 (dd, J=24.5, 10.1 Hz), 77.95 (d, J= 8.7 Hz), 74.30 (dd, J=12.3 Hz, 2.9 Hz), 71.31 (d, J=4.1 Hz), 70.25, 68.80. $^{31}$P-NMR (CDCl$_3$, 81 MHz): −14.35, −21.69.

Example 3

(S)-2-[(o-diphenylphosphino)phenyl]-1-difuryl-phosphinoferrocene (Ligand 2)

Sulfoxide (500 mg, 0.86 mmole) was dissolved in THF (12 ml) in a 50 ml round-bottomed flask with an argon inlet and the solution was cooled to −78° C. t-BuLi (1.07 ml, 1.71 mmole, 1.6 M in hexane) was then slowly added dropwise and stirred for 5 minutes at −78° C. Chlorodifurylphosphane (600 mg, 2.99 mmole) was added dropwise, the cooling bath was removed, and the reaction mixture was stirred for 30 minutes at RT. After quenching with saturated ammonium chloride solution (20 ml) the organic phase was separated and the aqueous phase was extracted with diethyl ether (2×50 ml). The combined organic phases were washed with sodium chloride solution (20 ml), dried over magnesium sulfate, filtered, and the solvent was distilled off on a rotary evaporator. The crude product was purified by column chromatography (n-pentane/diethyl ether 20:1). The diphosphane (239 mg, 0.39 mmole, 46% was obtained as a yellow solid (m.p.: 90° C.)

$^1$H-NMR (CDCl$_3$, 300 MHz): 8.19–8.14 (m, 1 H), 7.67–7.65 (m, 1 H), 7.40–7.33 (m, 2 H), 7.27–6.99 (m, 9 H), 6.83–6.72 (m, 4 H), 6.42–6.40 (m, 1 H), 6.32–6.31 (m, 1 H), 6.15–6.13 (m, 1 H), 4.47–4.46 (m, 1 H), 4.29–4.28 (m, 1 H), 4.12–4.09 (m, 1 H), 3.98 (s, 5 H).

$^{13}$C-NMR (CDCl$_3$, 75 MHz): 152.40 (d, J=11.6 Hz), 152.12 (d, J=4.7 Hz), 146.64 (d, J=2.4 Hz), 146.27 (d, J=3.0 Hz), 142.21 (d, J=1.8 Hz), 141.81 (d, J=1.2 Hz), 138.66 (d, J=13.4 Hz), 138.36 (d, J=14.0 Hz), 137.85 (d, J=12.8 Hz), 134.07–133.02 (m), 128.43–127.24 (m), 120.82 (d, J=25.6 Hz), 118.83 (dd, J=18.1, 4.1 Hz), 110.75 (d, J=6.4 Hz), 110.29 (d, J=4.1 Hz), 96.15 (dd, J=30.3, 10.6 Hz), 74.51 (d, J=3.5 Hz), 73.99 (dd, J=11.6, 5.5 Hz), 72.37 (d, J=5.3 Hz), 70.08, 69.08. $^{31}$P-NMR(CDCl$_3$, 81 MHz): −14.01 (d, J=2.3 Hz), −67.18 (d, J=2.3 Hz).

Examples of the asymmetric allylic alkylation of 3-acetoxy-1,3-diphenylpropene.

Example 4

Methyl(S,E)-2-carbomethoxy-3,5-diphenylpent-4-enoate

Allyl palladium chloride (dimer, 2.3 mg, 1.0 mole %) and (S)-2-[(o-diphenylphosphino)phenyl]-1-diphenyl-phosphinoferrocene (8.1 mg, 2.0 mole %) and (S)-2-[(o-diphenylphosphino)phenyl]-1-difurylphosphinoferrocene (7.8 mg, 2.0-mole %) were dissolved in dichloromethane (5 ml) under argon in a 50 ml capacity Schlenk vessel. After stirring for 15 minutes 3-acetoxy-1,3-diphenylpropene (168 mg, 0.64 mmole), N,O-bistrimethylsilyl acetamide (0.31 ml, 1.28 mmole), dimethyl malonate (0.14 ml, 1.28 mmole) and potassium acetate (3.2 mg, 0.03 mmole) were added. The reaction mixture was stirred at the above temperature for the specified time. After quenching the reaction with saturated ammonium chloride solution (20 ml) the reaction mixture was extracted with dichloromethane (2×50 ml), and the combined organic phases were washed with sodium chloride solution (20 ml) and dried over magnesium sulfate. After filtering the solution the solvent was distilled off on a rotary evaporator and the residue obtained was purified by column chromatography (n-pentane/diethyl ether 5:1). The malonate was obtained in the form of a colourless oil. The results obtained are summarised in Table 1.

The enantiomer excess was determined by high performance liquid chromatography (HPLC) (HPLC apparatus from the Dionex company with automated sample metering device and UV-VIS diode array detector, column: OD-H from Daicel Chemical Industries, eluent: n-heptane/i-PrOH 97:3, flow: 0.4 ml/min, detected wavelength: 215 nm):

HPLC (OD-H, 3% i-PrOH, 0.4 ml/min, 215 nm): tr/min=23.63 (R), 25.22 (S).

$^1$H-NMR (CDCl$_3$, 300 MHz): 7.27–7.06 (m, 10 H), 6.40 (d, J=15.8 Hz, 1 H), 6.25 (dd, J=8.4, 15.8 Hz, 1 H), 4.19 (dd, J=8.4, 10.9 Hz, 1 H), 3.88 (d, J=10.9 Hz, 1 H), 3.61 (s, 3 H), 3.43 (s, 3 H). $^{13}$C-NMR (CDCl$_3$, 75 MHz): 168.1, 167.7, 140.2, 136.8, 131.8, 129.1, 128.7, 128.4, 127.8, 127.5, 127.1, 126.3, 57.6, 52.5, 52.3, 49.1.

TABLE 1

| Ligand | Reaction Time [h] | Temperature [° C.] | Yield [%] | ee [%][a] |
|---|---|---|---|---|
| 1 | 3 | RT | 97 | 92.0 (S) |
| 1 | 4.5 | 0 | 98 | 95.0 (S) |
| 1 | 24 | −20 | 76 | 97.5 (S) |
| 2 | 22 | RT | 98 | 61.4 (S) |

[a]Absolute configuration in brackets

Example 5

Methyl(S,E)-2-carbomethoxy-3,5,5-triphenylpent-4-enoate

Sodium hydride (27.7 mg, 0.69 mmole) was suspended in THF (1.5 ml) under an argon atmosphere in a 25 ml Schlenk vessel, dimethyl malonate (91 mg, 0.69 mmole) was slowly added, and the reaction mixture was stirred for 2.5 hours at RT. Allyl palladium chloride (dimer, 4.0 mg, 2.5 mole %) and (S)-2-[(o-diphenylphosphino)phenyl]-1-diphenyl-phosphinoferrocene (28.8 mg, 10.0 mole %) were dissolved in THF (0.5 ml) under an argon atmosphere in a 50 ml Schlenk vessel. After stirring for 15 minutes 3-acetoxy-1,1,3-triphenylpropene (150 mg, 0.46 mmole) was added and the solution was stirred for 10 minutes. The suspension of the malonate was then added and the reaction mixture was stirred at the specified temperature for the specified time. After quenching the reaction with saturated ammonium chloride solution (20 ml) the reaction mixture was extracted with dichloromethane (2×50 ml), and the combined organic phases were washed with sodium chloride solution (20 ml) and dried over magnesium sulfate. After filtering the mixture the solvent was distilled off on a rotary evaporator and the residue obtained was purified by column chromatography (n-pentane/diethyl ether 8:1). The product was obtained in the form of a colourless solid. The results obtained are summarised in Table 2.

The enantiomer excess was determined by high performance liquid chromatography (HPLC) (HPLC apparatus from the Dionex company with automated sample metering device and UV-VIS diode array detector, column: OD from Daicel Chemical Industries, eluent: n-heptane/i-PrOH 99:1, flow: 0.6 ml/min, detected wavelength: 215 nm):

HPLC (OD, 1%/i-PrOH, 0.6 ml/min, 215 nm): tr/min=19.72 (S), 26.64 (R).

$^1$HNMR (CDCl$_3$, 300 MHz): 7.33–7.09 (m, 13 H), 7.01–6.99 (m, 2 H), 6.27 (d, J=10.8 Hz, 1 H), 4.15 (t, J=10.8 Hz, 1 H), 3.81 (d, J=10.2 Hz, 1 H), 3.61 (s, 3 H), 3.38 (s, 3 H). $^{13}$C-NMR(CDCl$_3$, 75 MHz): 168.07, 167.65, 143.71, 142.24, 141.21, 139.20, 129.70, 128.65, 128.15, 128.10, 127.80, 127.49, 127.45, 127.43, 126.90, 58.49, 52.48, 52.25, 45.20.

TABLE 2

| Ligand | Reaction Time [h] | Temperature [° C.] | Yield [%] | ee [%][a] |
|---|---|---|---|---|
| 1 | 24 | −20 | 76 | 97.5 (S) |
| 2 | 22 | RT | 98 | 61.4 (S) |

[a]Absolute configuration in brackets

Example 6

(−)-(E)-N-(1,3-diphenyl-2-propenyl)-4-toluenesulfonic acid amide

Potassium hydride (36.5 mg, 0.91 mmole) was suspended in THF (4 ml) under an argon atmosphere in a 25 ml Schlenk vessel, p-toluenesulfonamide (200 mg, 1.17 mmole) was added in portions and the reaction mixture was stirred for 2 hours at RT. Allyl palladium chloride (dimer, 2.3 mg, 1.0 mole %) and (S)-2-[(o-diphenylphosphino)phenyl]-1-diphenylphosphinoferrocene (8.1 mg, 2.0 mole %) and (S)-2-[(o-diphenylphosphino)phenyl]-1-difurylphosphinoferrocene (7.8 mg, 2 mole %) were dissolved in THF (1 ml) under an argon atmosphere in a 50 ml Schlenk vessel. After stirring for 15 minutes 3-acetoxy-1,3-diphenylpropene (168 mg, 0.64 mmole) and the suspension of the sulfonamide were added. The reaction mixture was stirred at the specified temperature for the specified time. After quenching the reaction with saturated ammonium chloride solution (20 ml) the reaction mixture was extracted with dichloromethane (2×50 ml), and the combined organic phases were washed with sodium chloride solution (20 ml) and dried over magnesium sulfate. After the mixture was filtered the solvent was distilled off on a rotary evaporator and the residue obtained was purified by column chromatography (n-pentane/diethyl ether 2:1). The product was obtained in the form of a colourless solid. The results obtained are summarised in Table 3.

The enantiomer-excess was determined by high performance liquid chromatography (HPLC) (HPLC apparatus from the Dionex company with automated sample metering device and UV-VIS diode array detector, column: OD from Daicel Chemical Industries, eluent: n-heptane/i-PrOH 90:10, flow: 0.5 ml/min, detected wavelength: 254 nm):

HPLC (OD, 10% i-PrOH, 0.5 ml/min, 254 nm): tr/min=33.01 (−)-enantiomer, 48.83 (+)-enantiomer.

$^1$H-NMR (CDCl$_3$, 300 MHz): 7.59–7.56 (m, 2 H), 7.20–7.03 (m, 12 H), 6.25 (d, J=15.9 Hz, 1 H), 5.99 (dd, J=15.6 Hz, 6.6 Hz, 1 H), 5.15 (br, d, J=7.5 Hz, 1 H), 5.03 (br, t, J=7.8 Hz, 1 H), 2.22 (s, 3 H). $^{13}$C-NMR (CDCl$_3$, 75 MHz): 143.18, 139.63, 137.71, 136.03, 132.03, 129.38, 128.65, 128.38, 128.15, 127.82, 127.77, 127.26, 127.01, 126.48, 59.72, 21.32.

TABLE 3

| Ligand | Reaction Time [h] | Temperature [° C.] | Yield [%] | ee [%][a] |
|---|---|---|---|---|
| 1 | 48 | −20 | 78 | 97.1 |
| 1 | 2.5 | RT | 96 | 94.0 |
| 2 | 72 | RT | 27 | 70.7 |

Example 7

(−)-(E)-N-(1,3-diphenyl-2-propenyl)-N'-benzoylhydrazine

Potassium hydride (36.5 mg, 0.91 mmole) was suspended in THF (4 ml) under an argon atmosphere in a 25 ml Schlenk vessel, benzhydrazide (159 mg, 1.17 mmole) was added in portions and the reaction mixture was stirred for 2 hours at RT. Allyl palladium chloride (dimer, 2.3 mg, 1.0 mole %) and (S)-2-[(o-diphenylphosphino)phenyl]-1-diphenylphosphinoferrocene (8.1 mg, 2.0 mole %) and (S)-2-[(o-diphenylphosphino)phenyl]-1-difurylphosphinoferrocene (7.8 mg, 2 mole %) were dissolved in THF (1 ml) under an argon atmosphere in a 25 ml Schlenk vessel. After stirring for 15 minutes 3-acetoxy-1,3-diphenylpropene (168 mg, 0.64 mmole) and the suspension of the sulfonamide were added. The reaction mixture was stirred at the specified temperature for the specified time. After quenching the reaction with saturated ammonium chloride solution (20 ml) the reaction mixture was extracted with dichloromethane (2×50 ml), and the combined organic phases were washed with sodium chloride solution (20 ml) and dried over magnesium sulfate. After the reaction mixture was filtered the solvent was distilled off on a rotary evaporator and the residue obtained was purified by column chromatography (n-pentane/diethyl ether 2:1). The product was obtained in the form of a colourless solid. The results obtained are summarised in Table 4.

The enantiomer excess was determined by high performance liquid chromatography (HPLC) (HPLC apparatus from the Dionex company with automated sample metering device and UV-VIS diode array detector, column: OD-H from Daicel Chemical Industries, eluent: n-heptane/i-PrOH 95:5, flow: 0.6 ml/min, detected wavelength: 254 nm):

HPLC (OD, 5% i-PrOH, 0.6 ml/min, 254 nm): tr/min=91.70 (−)-enantiomer, 106.76 (+)-enantiomer.

$^1$H-NMR (CDCl$_3$, 300 MHz): 7.64–7.11 (m, 17 H), 6.60 (d, J=15.6 Hz, 1 H), 630 (dd, J=15.6, 7.8 Hz, 1 H), 4.77 (d, J=7.8 Hz, 1 H). $^{13}$C-NMR (CDCl$_3$, 75 MHz): 167.39, 140.35, 136.53, 132.79, 132.61, 131.78, 129.40, 128.73, 128.60, 18.50, 127.88, 127.80, 127.74, 126.84, 126.52, 67.17.

TABLE 4

| Ligand | Reaction Time [h] | Temperature [° C.] | Yield [%] | ee [%]$^a$ |
|---|---|---|---|---|
| 1 | 24 | −20 | 98 | 95.1 |
| 1 | 1.5 | RT | 96 | 86.1 |
| 2 | 72 | RT | 70 | 78.7 |

Example 8

General Operating Procedure for the Hydrogenation of Acetamidocinnamic Acid Methyl Ester Derivatives 0.6 μmole of Rh(COD)$_2$OTf and 0.66 μmole of ligand are stirred for 10 minutes in 0.5 ml of methanol. 300 μmole of acetamidocinnamic acid methyl ester (in 1 ml of methanol) are metered into this solution. The reaction mixture is stirred for 16 hours at room temperature and under a hydrogen pressure of 5 bar in an autoclave. The reaction mixture is filtered through silica gel and the enantiomer excess is determined from the crude product by means of HPLC.

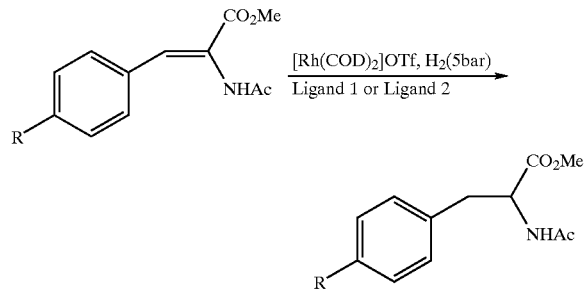

TABLE 5

| Ligand | R | % ee | Conversion (%) |
|---|---|---|---|
| 1 | H | 37 | 100 |
| 1 | Me | 13 | 96 |
| 1 | Br | 20 | 98 |
| 2 | H | 14 | 98 |
| 2 | Me | 10 | 98 |

Example 9

General Operating Procedure for the Hydrogenation of β-enamides

100 μl of a 0.05 M DMF solution of [Ru(C$_6$H$_6$)Cl$_2$]$_2$ (0.5 μmole) and 100 μl of a 0.01 M CH$_2$Cl$_2$ solution of Ligand 1 (1.0 μmole) are stirred for 10 minutes at 120° C. After cooling to room temperature, 400 μl of a 0.25 M MeOH solution of various β-enamides are added to this solution. The reaction mixture is stirred for 16–24 hours at room temperature and under a hydrogen pressure of 40 bar in an autoclave. The reaction mixture is filtered through silica gel, the solvent is removed, the residues are dissolved in isopropanol/hexane, and the enantiomer excess is then determined from the crude product by means of HPLC or GC (Chiralcel AD hexane/isopropanol 95/5 with 0.5% diethylamine).

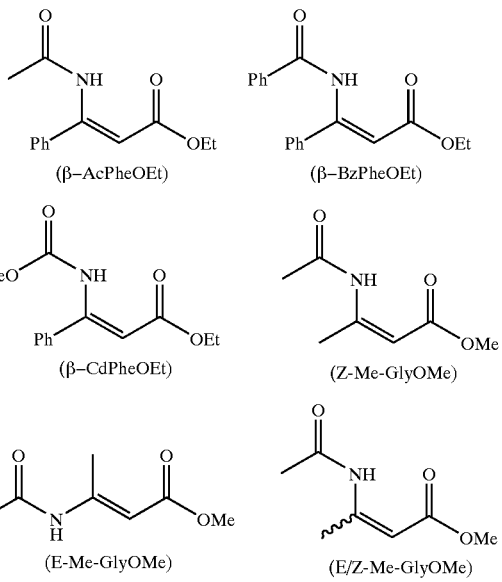

TABLE 6

| Substrate | Analysis Conditions | Conversion (%) | ee (%) |
|---|---|---|---|
| β-AcPheOEt | HPLC: Chiralcel OD; hexane/i-PrOH 93/7 with 0.5% trifluoroacetic acid | 98 | 60 |
| β-BzPheOEt | HPLC: Chiralcel OD; hexane/i-PrOH 88.4/11.6 with 0.5% trifluoroacetic acid | 99 | 51 |
| β-CbPheOEt | HPLC: Chiralcel OD; hexane/i-PrOH 83.4/16.6 with 0.5% trifluoroacetic acid | 79 | 77 |
| Z-Me-GlyOMe | GC: CB-Chiralsil DEX; isotherm 115° C. | 100 | 47 |
| E-Me-GlyOMe | GC: CB-Chiralsil DEX; isotherm 115° C. | 100 | 96 |
| Z/E-Me-GlyOMe | GC: CB-Chiralsil DEX; isotherm 115° C. | 100 | 14 |

Example 10

General Operating Procedure for the Hydrogenation of Keto Esters

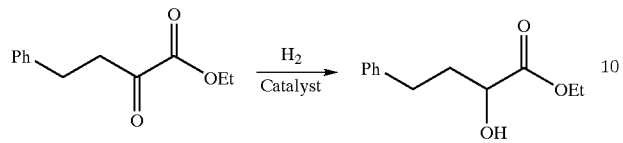

a) With [Ru(C$_6$H$_6$)Cl$_2$]$_2$:

50 μl of a 0.005 M DMF solution of [Ru(C$_6$H$_6$)Cl$_2$]$_2$ (0.25 μmole) and 110 μl of a 0.01 CH$_2$Cl$_2$ solution of ligand 1 (1.1 μmole) are stirred for 10 minutes at 120° C. After cooling to RT, 400 μl of a 0.25 M solution of ethyl 2-oxo-4-phenyl-butyrate are added to this solution. The reaction mixture is stirred for 16–20 hours at 60° C. and under a hydrogen pressure of 50 bar in an autoclave. The solvent is removed, the residues are dissolved in isopropanol/hexane, filtered through silica gel, and the enantiomer excess is determined from the crude product by means of HPLC or GC.

b) With [Ru(COD)$_2$]BF$_4$:

50 μl of a 0.01 M CH$_2$Cl$_2$ solution of [Ru(COD)$_2$]BF$_4$ (0.5 mmole) and 110 μl of a 0.01 M CH$_2$Cl$_2$ solution of ligand 1 (1.1 μmole) are stirred at room temperature for 15 minutes. 400 μl of a 0.25 M solution of ethyl 2-oxo-4-phenylbutyrate are added to this solution. The reaction mixture is stirred for 16–20 hours at 60° C. and under a hydrogen pressure of 50 bar in an autoclave. The solvents were evaporated, the residues were dissolved in isopropanol/hexane, filtered through silica gel, and the enantiomer excess is determined from the crude product by means of HPLC or GC.

c) With bis-2-(methylallyl)cycloocta-1,5-diene-ruthenium (II) [Ru(metallyl)$_2$COD]

50 μl of a 0.002 M CH$_2$Cl$_2$ solution of bis-2-(methylallyl)cycloocta-1,5-diene-ruthenium(II) (0.2 μl) and 110 μl of a 0.01 M CH$_2$Cl$_2$ solution of Ligand 1 (1.1 μmole) are stirred at room temperature for 10 minutes. 50 μl of a 0.04 M CH$_2$Cl$_2$ solution of HBF$_4$—OEt$_2$ were then added and stirred for 15 minutes. 400 μl of a 0.25 M CH$_2$Cl$_2$ solution of ketone were then added to this solution. The reaction mixture is stirred for 16–20 hours at room temperature and under a hydrogen pressure of 10 bar in an autoclave. The solvents were evaporated, the residues were dissolved in isopropanol/hexane, filtered through silica gel, and the enantiomer excess is determined from the crude product by means of HPLC or GC.

TABLE 7

| Solvent | Metal Complex | Conversion (%) | ee (%) |
| --- | --- | --- | --- |
| CH$_2$Cl$_2$ | Ru(metallyl)$_2$COD | 9 | 35 |
| CH$_2$Cl$_2$ | [Rh(COD)$_2$]BF$_4$ | 5 | 10 |
| CH$_2$Cl$_2$ | [Ru(C$_6$H$_6$)Cl$_2$]$_2$ | 100 | 89 |
| THF | [Rh(COD)$_2$]BF$_4$ | 22 | 26 |
| THF | [Ru(C$_6$H$_6$)Cl$_2$]$_2$ | 100 | 88 |
| MeOH | [Ru(C$_6$H$_6$)Cl$_2$]$_2$ | 48 | 57 |

The invention claimed is:

1. Bidentate organophosphorus ligand of the formula (I)

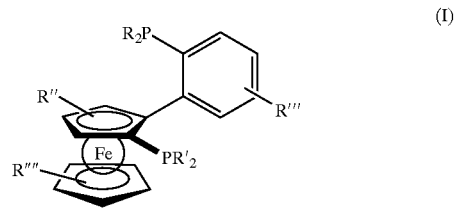

(I)

wherein

R, R' independently of one another for each of the two substituents R and independently of one another for each of the two substituents R' may denote a radical selected from the group C$_1$–C$_{24}$ alkyl, C$_2$–C$_{24}$ alkenyl, C$_3$–C$_8$ cycloalkyl, C$_3$–C$_8$ cycloalkenyl, C$_6$–C$_{14}$ aryl, phenyl, naphthyl, fluorenyl, furfuryl, 1-adamantyl, C$_2$–C$_{13}$ heteroaryl, in which the number of heteroatoms from the group N, O, S, may be 1 to 4, and in which the aforementioned substituents R and R' may in each case be monosubstituted or polysubstituted, wherein these substituents may independently of one another be selected from the group C$_1$–C$_{12}$ alkyl, C$_2$–C$_{12}$ alkenyl, C$_1$–C$_{10}$ haloalkyl, C$_3$–C$_8$ cycloalkyl, C$_3$–C$_8$ cycloalkenyl, C$_2$–C$_9$ heteroalkyl, C$_1$–C$_9$ heteroalkenyl, C$_6$–C$_{14}$ aryl, phenyl, naphthyl, fluorenyl, C$_2$–C$_7$ heteroaryl, in which the number of heteroatoms from the group N, O, S, may be 1 to 4, C$_1$–C$_{10}$ alkoxy, C$_1$–C$_9$ trihalomethylalkyl, trifluoromethyl, trichloromethyl, fluoro, chloro, hydroxy, C$_1$–C$_8$ substituted amino of the forms mono-, di-, tri- C$_1$–C$_8$ alkylamino or C$_2$–C$_8$ alkenylamino or mono-, di-, tri- C$_6$–C$_8$ arylamino or carboxyl, carboxylato of the form COOR"" where R"" denotes a monovalent cation or a C$_1$–C$_8$ alkyl, C$_1$–C$_8$ acyloxy, tri- C$_1$–C$_6$ alkylsilyl, and in which two of these substituents may also be bridged, and wherein R", R"', R"" independently of one another may for each of the substituents R", R"' or R"" denote a radical selected from the group hydrogen, C$_1$–C$_{24}$ alkyl, C$_2$–C$_{24}$ alkenyl, C$_3$–C$_8$ cycloalkyl, C$_3$–C$_8$ cycloalkenyl, C$_1$–C$_{10}$ alkoxy, C$_{1-C9}$ trihalomethylalkyl, trifluoromethyl, trichloromethyl, fluoro, chloro, hydroxy, C$_1$–C$_8$ substituted amino of the forms mono-, di-, tri- C$_1$–C$_8$ alkylamino or C$_2$–C$_8$ alkenylamino or mono-, di-, tri- C$_6$–C$_8$ arylamino or carboxyl, carboxylato of the form COOR"", where R"" denotes a monovalent cation or a C$_1$–C$_8$ alkyl or C$_1$–C$_8$ acyloxy, tri- C$_1$–C$_6$ alkylsilyl, and where two of these substituents may also be bridged.

2. The bidentate organophosphorus ligand according to claim 1, wherein R and R' independently of one another may be phenyl, furfuryl, 3,5-dimethylphenyl, 4-methylphenyl, 2-methylphenyl, 4-methoxyphenyl, 3,5-bis(trifluoromethyl) phenyl, cyclohexyl, tert-butyl, n-butyl, 2-propyl, ethyl, methyl or 1-adamantyl.

3. The bidentate organophosphorus ligand according to claim 1, wherein characterized in that the compound of the formula (I) is optically active.

4. The bidentate organophosphorus ligand according to claim 1, wherein the compound of the formula (I) is enantiomer-enriched.

5. A complex compound containing at least one ligand according to claim 1 and at least one transition metal.

6. The complex compound according to claim 5, wherein the complex compound contains at least one transition metal atom or ion selected from the group consisting of palladium, platinum, rhodium, ruthenium, osmium, iridium, cobalt, nickel, copper and mixtures thereof.

7. The complex compound according to claim 5, obtained by reacting a metal salt or a corresponding precomplex with one or more ligands of the general formula (I).

8. A method of performing asymmetric reactions or polymerizations, comprising, adding to a reaction vessel, a complex compound according to claim 5, as a catalyst.

9. A method of performing a reaction, comprising, adding to a reaction vessel, a complex compound according to claim 5, as a catalyst, and
wherein, the reaction is selected from asymmetric hydrogenations, hydroformylations, rearrangements, allylic alkylations, cyclopropanations, hydrosilylations, hydride transfer reactions, hydroborations, hydrocyanations, hydrocarboxylations, aldol reactions or Heck reactions.

10. A process for the production of one or more ligands of the formula (I) according to claim 1, comprising the following synthesis steps:
 i. lithiation and transmetallation of chiral ferrocenyl sulfoxide in the presence of a lithium base and in the presence of $ZnBr_2$,
 ii. reaction of the ferrocenyl sulfoxide A with 1-iodophosphinobenzene in the presence of a palladium catalyst, and
 iii. substitution of the sulfoxide group by a $HalPR'_2$ in the presence of a strong lithium base, in which Hal may denote Cl or Br.

11. A complex compound containing at least one ligand according to claim 2 and at least one transition metal.

12. A complex compound containing at least one ligand according to claim 3 and at least one transition metal.

13. A complex compound containing at least one ligand according to claim 4 and at least one transition metal.

14. The complex compound according to claim 11, wherein the complex compound contains at least one transition metal atom or ion selected from the group consisting of palladium, platinum, rhodium, ruthenium, osmium, iridium, cobalt, nickel, copper and mixtures thereof.

15. The complex compound according to claim 12, wherein the complex compound contains at least one transition metal atom or ion selected from the group consisting of palladium, platinum, rhodium, ruthenium, osmium, iridium, cobalt, nickel, copper and mixtures thereof.

16. The complex compound according to claim 13, wherein the complex compound contains at least one transition metal atom or ion selected from the group consisting of palladium, platinum, rhodium, ruthenium, osmium, iridium, cobalt, nickel, copper and mixtures thereof.

17. The complex compound according to claim 6, obtained by reacting a metal salt or a corresponding precomplex with one or more ligands of the general formula (I).

18. A method of performing asymmetric reactions or polymerizations, comprising, adding to a reaction vessel, a complex compound according to claim 6, as a catalyst.

19. A method of performing asymmetric reactions or polymerizations, comprising, adding to a reaction vessel, a complex compound according to claim 7, as a catalyst.

20. A method of performing a reaction, comprising, adding to a reaction vessel, a complex compound according to claim 6, as a catalyst, and
wherein, the reaction is selected from asymmetric hydrogenations, hydroformylations, rearrangements, allylic alkylations, cyclopropanations, hydrosilylations, hydride transfer reactions, hydroborations, hydrocyanations, hydrocarboxylations, aldol reactions or Heck reactions.

\* \* \* \* \*